(12) United States Patent
Coffey et al.

(10) Patent No.: US 6,808,916 B2
(45) Date of Patent: Oct. 26, 2004

(54) METHOD OF EXTRACTING VIRUS FROM CELL CULTURE

(75) Inventors: Matthew C. Coffey, Calgary (CA); Bradley G. Thompson, Calgary (CA)

(73) Assignee: Oncolytics Biotech Inc., Calgary (CA)

( * ) Notice: Subject to any disclaimer, the term of this patent is extended or adjusted under 35 U.S.C. 154(b) by 6 days.

(21) Appl. No.: 10/097,183

(22) Filed: Mar. 14, 2002

(65) Prior Publication Data

US 2002/0168764 A1 Nov. 14, 2002

Related U.S. Application Data

(60) Provisional application No. 60/276,734, filed on Mar. 16, 2001.

(51) Int. Cl.$^7$ ............................ C12N 7/06; A61K 39/15
(52) U.S. Cl. .................... 435/238; 435/235.1; 435/239; 424/215.1
(58) Field of Search ............................. 435/235.1, 238, 435/239; 424/215.1

(56) References Cited

U.S. PATENT DOCUMENTS

| | | | |
|---|---|---|---|
| 6,146,873 A | * | 11/2000 | Kistner et al. ........... 435/235.1 |
| 6,194,191 B1 | | 2/2001 | Cho et al. |
| 6,528,305 B2 | * | 3/2003 | Thompson et al. ......... 435/325 |
| 2002/0037576 A1 | | 3/2002 | Thompson et al. |

FOREIGN PATENT DOCUMENTS

| | | |
|---|---|---|
| JP | 63044532 A | 2/1988 |
| WO | WO99/08692 A1 | 2/1999 |
| WO | WO 02/12435 A1 | 2/2002 |

OTHER PUBLICATIONS

Berry et al., Biotechnology and Bioengineering, "Production of Reovirus Type–1 and Type–3 from Vero Cells Grown on Solid and Macroporous Microcarriers", *Biotechnology and Biogengineering* 62: 12–19 (1999).
Bos, J.L., "Ras Oncogenes in Human Cancer: A Review", *Canc. Res.* 49(17): 4682–4689 (1989).
Chandron and Nibert, "Protease cleavage of reovirus capsid protein mu1 and mu1C is blocked by alkyl sulfate detergents, yielding a new type of infectious subvirion particle", *J. of Virology* 72(1):467–75 (1998).
Coffey, M.C., et al., "Reovirus therapy of tumors with activated Ras pathway", *Science* 282: 1332–1334 (1998).
Drastini, Y. et al., "Comparison of eight different [procedures for harvesting avian reoviruses grown in Vero cells", *J. Virological Methods* 39: 269–278 (1992).
McCrae, M.A. and Joklik, W.K., "The nature of the polypeptide encoded by each of the 10 double–stranded RNA segments of reovirus type 3", *Virology*, 89:578–593 (1979).
Smith, R.E., et al., "Polypeptide components of virions, top component and cores of reovirus type 3", *Virology*, 39:791–810 (1969).
Strong, J.E. and P.W. Lee, "The v–erbV oncogene confers enhanced cellular susceptibility to reovirus infection", *J. Virol.* 70: 612–616 (1996).
Strong, J.E., et al., "Evidence that the Epidermal Growth Factor Receptor on Host Cells Confers Reovirus Infection Efficiency", *Virology* 197(1): 405–411 (1993).
Strong, J.E., et al., "The molecular basis of viral oncolysis: usurpation of the Ras signaling pathway by reovirus", *EMBO J.* 17: 3351–3362 (1998).
Taber et al., "The selection of virus–resistant Chinese hamster ovary cells", *Cell* 8: 529–533 (1976).
Hitt, Mary et al., "Construction and propagation of human adenovirus vectors", *Cell Biology* 1(3):500–512 (1998).
Nibert, Max L. et al., "Reoviruses and their replication", *Fundamental Virology* Third Edition, 691–730 (1996).
Drayna, D. et al., "Genetic Studies on the Mechanism of Chemical and Physical Inactivation of Reovirus" *J General Virology* 63(1):149–160 (1982).
Mendez, Israel et al., "A comparative analysis of Freon substitutes in the purification of reovirus and calicivirus", *J Virological Methods* 90(1):59–67 (2000).
Mora, M. et al., "Association of Reovirus Proteins with the Structural Matrix of Infected Cells", *Virology* 159(2):265–277 (1987).

\* cited by examiner

Primary Examiner—James Housel
Assistant Examiner—Stacy B. Chen
(74) *Attorney, Agent, or Firm*—Fish & Richardson P.C.

(57) ABSTRACT

The present invention is directed to a method of extracting virus, particularly reovirus, from a culture of cells. Infectious virus can be extracted from the culture with a detergent at a convenient temperature such as 25° C. or 37° C. to produce high virus titers. Both ionic and non-ionic detergents can be used in the present invention.

19 Claims, No Drawings

METHOD OF EXTRACTING VIRUS FROM CELL CULTURE

RELATED APPLICATIONS

This application claims the benefit of U.S. Provisional Applications Ser. No. 60/276,734, filed Mar. 16, 2001, the entire disclosure of which is hereby incorporated by reference.

FIELD OF THE INVENTION

This invention relates to a method of extracting virus from a cell culture. In particular, the method is useful to extract infectious virus which is suitable for clinical administration to mammals, including human.

REFERENCES

Berry et al., Biotechnology and Bioengineering, "Production of Reovirus Type-1 and Type-3 from Vero Cells Grown on Solid and Macroporous Microcarriers", *Biotechnology and Bioengineering* 62: 12–19 (1999).
Bos, J. L., "Ras Oncogenes in Human Cancer: A Review", *Canc. Res.* 49(17): 4682–4689 (1989).
Chandron and Nibert, "Protease cleavage of reovirus capsid protein mu1 and mu1C is blocked by alkyl sulfate detergents, yielding a new type of infectious subvirion particle", *J. of Virology* 72(1):467–75 (1998).
Coffey, M. C., et al., "Reovirus therapy of tumors with activated Ras pathway", *Science* 282: 1332–1334 (1998).
Davis, et al., Microbiology, Lippincott, Philadelphia (1990).
Drastini, Y. et al., "Comparison of eight different [procedures for harvesting avian reoviruses grown in Vero cells", *J. Virological Methods* 39: 269–278 (1992).
Fields, B. N. et al., *Fundamental Virology*, 3rd Edition, Lippincott-Raven (1996).
Japanese Patent 63044532A, published Feb. 25, 1988.
McRae, M. A. and Joklik, W. K., "The nature of the polypeptide encoded by each of the 10 double-stranded RNA segments of reovirus type 3", *Virology*, 89:578–593 (1979).
Nibert et al., "Reovirus and their replication", in Fields et al., *Fundamental Virology*, 3rd Edition, Lippincott-Raven (1996).
*Remington's Pharmaceutical Sciences*, Mace Publishing Company, Philadelphia Pa. 19th ed. (1995).
Smith, R. E., et al., "Polypeptide components of virions, top component and cores of reovirus type 3", *Virology*, 39:791–800 (1969).
Strong, J. E. and P. W. Lee, "The v-erbV oncogene confers enhanced cellular susceptibility to reovirus infection", *J. Virol.* 70: 612–616 (1996).
Strong, J. E., et al., "Evidence that the Epidermal Growth Factor Receptor on Host Cells Confers Reovirus Infection Efficiency", *Virology* 197(1): 405–411 (1993).
Strong, J. E., et al., "The molecular basis of viral oncolysis: usurpation of the Ras signaling pathway by reovirus", *EMBO J.* 17: 3351–3362 (1998).
Taber et al., "The selection of virus-resistant Chinese hamster ovary cells", Cell 8: 529-533 (1976).
WO99/08692A1, published Feb. 25, 1999.

All of the above publications, patents and patent applications are herein incorporated by reference in their entirety to the same extent as if the disclosure of each individual publication, patent application or patent was specifically and individually indicated to be incorporated by reference in its entirety.

BACKGROUND OF THE INVENTION

Due to the vast number of diseases caused by viruses, virology has been an intensively studied field. There has always been the demand to produce viruses efficiently in order to isolate and purify viral proteins, to generate vaccines, or to provide infectious viruses for laboratory studies. Recently, the new development of virus therapy has further necessitated the need for efficient production of infectious viruses.

Reovirus therapy is an example of virus therapy. Reovirus is a double-stranded RNA virus capable of binding to a multitude of cells. However, most cells are not susceptible to reovirus infection and binding of reovirus to its cellular receptor results in no viral replication or virus particle production. This is probably the reason why reovirus is not known to be associated with any particular disease.

It was discovered recently that cells transformed with the ras oncogene become susceptible to reovirus infection, while their untransformed counterparts are not (Strong et al., 1998). For example, when reovirus-resistant NIH 3T3 cells were transformed with activated Ras or Sos, a protein which activates Ras, reovirus infection was enhanced. Similarly, mouse fibroblasts that are resistant to reovirus infection became susceptible after transfection with the EGF receptor gene or the v-erbB oncogene, both of which activate the ras pathway (Strong et al., 1993; Strong et al., 1996). Thus, reovirus can selectively infect and replicate in cells with an activated Ras pathway.

The ras oncogene accounts for a large percentage of mammalian tumors. Activating mutations of the ras gene itself occur in about 30% of all human tumors (Bos, 1989), primarily in pancreatic (90%), sporadic colorectal (50%) and lung (40%) carcinomas, as well as myeloid leukemia (30%). Activation of factors upstream or downstream of ras in the ras pathway is also associated with tumor. For example, overexpression of HER2/Neu/ErbB2 or the epidermal growth factor (EGF) receptor is common in breast cancer (25–30%), and overexpression of platelet-derived growth factor (PDGF) receptor or EGF receptor is prevalent in gliomas and glioblastomas (40–50%). EGF receptor and PDGF receptor are both known to activate ras upon binding to their respective ligand, and v-erbB encodes a constitutively activated receptor lacking the extracellular domain.

Since a large number of human tumors are accounted for by genetic alteration of the proto-oncogene ras or a high Ras activity, reovirus therapy is a new, promising therapy for such conditions (Coffey et al., 1998). Reovirus therapy is highly selective for Ras-associated tumor cells and leaves normal cells uninfected. This therapy has wide applications and can be used in both human and non-human animals.

In order to produce reovirus suitable for clinical administration, fast and efficient methods of producing reovirus in cultured cells are needed. Moreover, the traditional method of extracting viruses from cultured cells is tedious and time consuming, rendering the cost of virus production too high. Therefore, an improved method for virus extraction is also needed.

SUMMARY OF THE INVENTION

The present invention is directed to a method of extracting virus from a culture of cells. Viruses are traditionally extracted from cells by multiple rounds of freeze-thawing, followed by purification with density gradients and ultracentrifugation. In the present invention, we extracted virus from a culture of cells with a detergent and the resulting yields were better than those obtained by freeze-thawing. Moreover, this extraction step can be performed at or above ambient temperature. In particular, the extraction can take place at a convenient temperature such as 25° C. or 37° C. and still produce high virus titers.

Accordingly, one aspect of the invention provides a method of producing virus from a culture of cells, comprising the steps of:

(a) providing a culture of cells which has been infected by the virus;

(b) extracting the virus from the cells by adding a detergent to the culture; and (c) collecting the virus.

The detergent may be any detergent commonly used for the disruption of cells. Particularly, the detergent is selected from the group consisting of octoxynol-9 to 10 (Triton X-100), polyethylene glycol sorbitan monolaurate (Tween 20), octylphenoxy polyethoxy ethanol (NP-40) and sodium deoxycholate. The detergent is most preferably Triton X-100, particularly at a final concentration of 1%.

This virus extraction method can be performed at any temperature above freezing, particularly above 4° C. Typically, the extraction can be conveniently performed at ambient temperature, without having to maintain a preselected temperature. Preferably, the extraction is performed at 25° C. More preferably the extraction is performed at the same temperature as the cells are cultured, for example 37° C., such that the cell culture and virus extraction can be performed in the same incubator.

The cell culture is incubated with the detergent for a period of time sufficient to disrupt the cells. The incubation period is preferably 60 minutes or less, more preferably 30 minutes or less, and most preferably 10 minutes.

In a preferred embodiment, the virus is a non-enveloped virus. The non-enveloped virus is preferably a reovirus. The present invention can be applied to any reovirus, particularly mammalian reoviruses. The mammalian reovirus is preferably a human reovirus, more preferably a serotype 3 reovirus, and most preferably the Dearing strain reovirus.

The cells may be any cells useful to produce the virus of interest, including adherent cells or suspension cells. Preferably, the cells are grown in a suspension culture. When the virus is reovirus, the cell is preferably HEK 293 cells.

After extraction, the virus is collected. Cell debris can be removed, for example, by filtration. To increase the flow rate of filtration, stepwise filtration can be performed wherein prefiltration with a larger pore size is followed by at least one filtration step with a smaller pore size. The pore size and type of filters depend on nature of the virus and cells, and can be determined by people with ordinary skills in the art. For example, for reovirus production using HEK 293/SF cells, a prefilter of 8 or 5 $\mu$M pore size can be used, followed by a 3 $\mu$M filter, and finally a 0.8 $\mu$M filter.

The filtrate can further be concentrated to reduce the volume of the virus suspension. If it is desired to change the solution virus is suspended in, methods such as ion exchange chromatography or dialysis can be employed.

Another aspect of the present invention provides a composition which comprises the virus collected according to the present invention. In particular, viral compositions suitable for clinical administrations are provided. Preferably, the virus is reovirus. The composition may further comprise a pharmaceutically acceptable excipient and/or carrier.

DETAILED DESCRIPTION OF THE INVENTION

The present invention is directed to a method of extracting virus from a culture of cells. Instead of the traditional freeze-thawing technique, we have developed a fast and simple method which can be performed conveniently.

Prior to describing the invention in further detail, the terms used in this application are defined as follows unless otherwise indicated.

Definitions

As used herein, "viral infection" refers to the entry of a virus into a cell and the subsequent replication of the virus in the cell.

As used herein, "multiplicity of infection" refers to the ratio of the number of virus to the number of cells when a virus is used to contact cells.

As used herein, "cell lysis" refers to the disruption of cell membrane of a cell and the subsequent release of all or part of the content of the cell.

As used herein, "culture conditions" refer to the conditions used in a cell culture, including but not limited to the temperature, type of culture containers, humidity, concentration of $CO_2$ or any other gas used in the culture containers, type of the culture medium, the initial density of the cultured cells, and if the cells are infected with a virus, the initial multiplicity of infection.

As used herein, a "cell culture" or "culture of cells" means a population of cultured cells as found in their culture conditions. In particular, a cell culture includes the cells and the culture medium. Cells that have been pelleted are not considered a cell culture unless they are placed in the culture conditions again.

As used herein, a virus that is "cell associated" refers to a virus which is attached to or trapped in part of a cell in which the virus has been produced. Thus, a virus is cell associated before the host cell is lysed. When cell lysis begins, a virus may be still attached to or trapped in part of the broken cell and remain cell associated. However, when the virus is released free into the medium, it is not cell associated anymore. A "cell free virus" is a virus which is not cell associated.

As used herein, "extracting" a virus refers to the act of converting a cell-associated virus into a cell free virus.

As used herein, a "detergent" is a substance having a hydrophilic end and a hydrophobic end. The detergent is preferably a synthetic chemical compound and more preferably a biodegradable synthetic chemical compound. The detergent useful in the present invention enhances disruption of cell membranes to facilitate release of the content of the disrupted cells.

As used herein, "incubating" after addition of a detergent to a cell culture refers to the act of allowing the cell culture to be mixed with the detergent.

As used herein, "collecting" the virus refers to the act of collecting the produced virus from a cell culture which has been previously infected with the virus. The virus is typically collected by separating cellular debris from the virus and harvest the portion which comprises the virus. Optionally, the virus can be further separated from the soluble substances, e.g., by centrifugation.

As used herein, "ambient temperature" refers to a temperature between about 10° C. and about 30° C. Ambient temperature is preferably between about 15° C. and about 30° C., more preferably between about 20° C. and about 25° C., and most preferably about 25° C.

As used herein, "cytopathic effect" is indicated by the cells becoming swollen and granular in appearance and the cell clumps breaking up. The cells which show a cytopathic effect stain negative in a viable cell count because they will take up the staining dye.

As used herein, "adherent cells" refer to cells which adhere to the culture containers in a cell culture. Examples of adherent cells include monolayer cells, which are cells that form a single layer of cells on the surface of a culture container. "Suspension cells" or "suspended cells" refer to cells which do not adhere to culture containers in a cell culture. Suspension cells can be grown in a "spin culture", which is a culture in which the culture medium is stirred continuously during the culture process.

As used herein, a cell is "disrupted" when the cell membrane is ruptured and at least some of the cell content is released from the cell. A cell may be disrupted, for example, by freeze-thawing, sonication or detergent treatments.

As used herein, "viability of the cells" or "percentage of cells remaining viable" is the percentage of the cells which do not show a cytopathic effect in a population.

As used herein, a "non-enveloped virus" is a virus which does not have an envelope. For example, a non-enveloped virus may be any virus which belongs to the family of Adenoviridae (e.g. adenovirus), Picornaviridae (e.g. polio virus), Reovirudae (e.g. reovirus), Papovarviridae (e.g. papilloma virus), Parvoviridae (e.g. Kilham rat virus) or Iridoviridae (e.g. tipula iridescent virus).

As used herein, "reovirus" refers to any virus classified in the reovirus genus, whether naturally occurring, modified or recombinant. Reoviruses are viruses with a double-stranded, segmented RNA genome. The virions measure 60–80 nm in diameter and possess two concentric capsid shells, each of which is icosahedral. The genome consists of double-stranded RNA in 10–12 discrete segments with a total genome size of 16–27 kbp. The individual RNA segments vary in size. Three distinct but related types of reovirus have been recovered from many species. All three types share a common complement-fixing antigen.

The human reovirus consists of three serotypes: type 1 (strain Lang or T1L), type 2 (strain Jones, T2J) and type 3 (strain Dearing or strain Abney, T3D). The three serotypes are easily identifiable on the basis of neutralization and hemagglutinin-inhibition assays (see, for example, Fields, B. N. et al., 1996).

The reovirus may be naturally occurring or modified. The reovirus is "naturally-occurring" when it can be isolated from a source in nature and has not been intentionally modified by humans in the laboratory. For example, the reovirus can be from a "field source", that is, from a human who has been infected with the reovirus.

The reovirus may be modified but still capable of lytically infecting a mammalian cell having an active ras pathway. The reovirus may be chemically or biochemically pretreated (e.g., by treatment with a protease, such as chymotrypsin or trypsin) prior to administration to the proliferating cells. Pretreatment with a protease removes the outer coat or capsid of the virus and may increase the infectivity of the virus. The reovirus may be coated in a liposome or micelle (Chandron and Nibert, 1998). For example, the virion may be treated with chymotrypsin in the presence of micelle forming concentrations of alkyl sulfate detergents to generate a new infectious subvirion particle.

The reovirus may be a recombinant (i.e. reasserted) reovirus from two or more types of reoviruses with differing pathogenic phenotypes such that it contains different antigenic determinants, thereby reducing or preventing an immune response by a mammal previously exposed to a reovirus subtype. Such recombinant virions can be generated by co-infection of mammalian cells with different subtypes of reovirus with the resulting resorting and incorporation of different subtype coat proteins into the resulting virion capsids.

As used herein, "HEK 293 cells" refer to the human embryo kidney cell line designated 293 (ATCC Number CRL-1573) or its derivatives. For example, 293/SF cells (ATCC Number CRL-1573.1) are HEK 293 cells which have been adapted to grow in serum-free media. Also contemplated in this invention are HEK 293 cells adapted to grow in other culture conditions, or any kind of HEK 293 cells or derivatives which are transformed with an exogenous DNA, provided that this transformation does not impair the ability of the cells to support efficient reovirus production as described in this invention.

As used herein, "clinical administration" of a substance refers to contacting any part of the body of a living organism with the substance in order to improve or maintain the organism's health conditions.

Method

Reovirus is used as a model system to describe the present invention in detail.

However, it is contemplated that the present invention can be applied to other viruses as well, particularly other non-enveloped viruses.

We have previously developed a method to grow reovirus in HEK 293 cells. Reovirus replicates in HEK 293 cells to yield a high titer of virus in the cells shortly after virus infection, thereby providing a simple and efficient method of producing reovirus (Examples 1 and 2). In addition, HEK 293 cells has been adapted to grow in suspension which can be cultured in large quantity, and we developed a large scale production method. To isolate reovirus from the suspension culture, we initially followed traditional methods to extract and purify viral particles. Briefly, the cells were disrupted by freeze-thawing and extracted by Freon three times. The viral particles were then purified with a CsCl gradient and ultracentrifugation. However, this protocol was too tedious and time consuming for large scale virus production.

We therefore developed a simplified method to extract the reovirus. It was discovered that by incubating the HEK 293 cell culture with a detergent for a short period of time, high levels of infectious reovirus were released to the extract. The virus can then be separated from the cell debris with a simple separation method based on size or density difference such as filtration, diafiltration or size exclusion, and the resulting virus can be used for reovirus therapy. The reovirus produced according to the present invention is suitable for administrations in human, and this protocol is consistent with the FDA recommendation of disrupting cells in the presence of a detergent.

We tested four detergents in the present invention. The non-ionic detergents Triton X-100, NP-40 and Tween 20, as well as the ionic detergent sodium deoxycholate. While all four functioned in the present invention, Triton X-100 repeatedly yielded more virus than the other two non-ionic detergents by about 2 fold. Sodium deoxycholate was about as effective as Triton X-100. It is contemplated that other detergents, particularly the ones commonly used to disrupt cells, can be used in the present invention as well. Examples of these other detergents include the other Triton detergents, the other Tween detergents (e.g. Tween-80), sodium dodecyl sulfate, lithium dodecyl sulfate, and dodecyltrimethylammonium chloride.

The results indicate that detergent extraction was more effective than freeze-thawing, the standard procedure for virus extraction. It has been reported that to extract avian reovirus from Vero cells, in which the reovirus is highly cell associated, distilled deionized water was more effective than freeze-thawing, freon extraction or trypsin treatment (Drastini et al., 1992). The present invention provides a more rapid and convenient yet effective approach, because there is no need to pellet and then resuspend the cells as required by the distilled water method.

It is contemplated that high concentrations of salt, such as guanidine chloride, can be used in the present invention to substitute for detergents. However, it is preferable to use detergents rather than high concentrations of salt.

The present invention thus provides a fast and simple method of extracting viruses from a cell culture. The detergent can be added directly to a suspension culture or to the medium of adherent cells. In either case, the medium does not need to be removed first. Furthermore, no other means of disrupting cells or extracting viruses is necessary, such as free-thawing or sonication.

An important feature of the present invention is that the extraction procedure can be performed at or above ambient temperature. Traditionally, virus extraction and purification are carried out at a low temperature, typically 0–4° C., to preserve the structures and functions of proteins. For the same reason, protease inhibitors are usually also included in the extraction solutions. Therefore, it is surprising that the present protocol can be conducted at a higher temperature without any protease inhibitor. In fact, a temperature as high as 37° C. resulted in about the same amount of infectious virus as 25° C. (Table 3). Consequently, virus extraction can be carried out by adding a detergent directly to the cell culture and continuing to agitate the culture in order to release the virus, without having to change the temperature. Alternatively, since there is no need to maintain a constant temperature for virus extraction according to the present invention, the procedure can take place at ambient temperature even though ambient temperature may vary from place to place or with time in the same place.

After extraction, the virus can be collected. Any methods established in the art can be used to purify the virus. For example, cell debris can be removed by filtration. To increase the flow rate of filtration, stepwise filtration can be performed wherein prefiltration with a larger pore size is followed by at least one filtration step with a smaller pore size. The pore size and type of filters depend on nature of the virus and cells, and can be determined by people with ordinary skills in the art. For example, for reovirus production using HEK 293/SF cells, a prefilter of 8 or 5 $\mu$M pore size can be used, followed by a 3 $\mu$M filter, and finally a 0.8 $\mu$M filter.

If the volume of the filtrate is too large, the filtrate can then be concentrated by any method known in the art. For example, ultrafiltration can be performed using the hollow fiber cartridge (A/G Technology) or the plate and frame cassette (Pall Filtron). The concentrated virus suspension can be further subjected to dialysis or ion exchange chromatography to remove excess salt or add additional ingredients into the virus suspension.

The present method can be applied to reovirus produced from cells other than HEK 293 cells, including but not limited to, mouse L929, Vero and Chinese hamster ovary cells. It is contemplated that the present method be applied to other viruses as well, particularly the other non-enveloped viruses.

Compositions

Also provided are virus compositions prepared according to the present invention. These compositions can be used in the isolation and characterization of viral proteins, production of vaccines, or, where the composition contains infectious virus, as virus stocks or in clinical administration.

For the purpose of clinical administration, the composition is usually mixed with an excipient, diluted by an excipient or enclosed within such a carrier which can be in the form of a capsule, sachet, paper or other container (WO99/08692A1). When the pharmaceutically acceptable excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

For preparing solid compositions such as tablets, the principal active ingredient/freovirus is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

Another preferred formulation employed in the methods of the present invention employs transdermal delivery devices ("patches"). Such transdermal patches may be used to provide continuous or discontinuous infusion of the reovirus of the present invention in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on demand delivery of pharmaceutical agents.

Other suitable formulations for use in the present invention can be found in *Remington's Pharmaceutical Sciences*.

The following examples are offered to illustrate this invention and are not to be construed in any way as limiting the scope of the present invention.

EXAMPLES

In the examples below, the following abbreviations have the following meanings. Abbreviations not defined have their generally accepted meanings.

| | | |
|---|---|---|
| CI | = | Confidence Interval |
| $TCID_{50}$ | = | Tissue Culture Infectious $Dose_{50}$ |
| $\mu M$ | = | micromolar |
| mM | = | millimolar |
| M | = | molar |
| ml | = | milliliter |
| $\mu l$ | = | microliter |
| mg | = | milligram |
| $\mu g$ | = | microgram |
| g/L | = | grams per liter |
| rpm | = | revolutions per minute |
| FBS | = | fetal bovine serum |
| DTT | = | dithiothrietol |
| NP-40 | = | Nonidet P-40 (Octylphenoxy Polyethoxy Ethanol) |
| SDS | = | sodium dodecyl sulfate |
| PBS | = | phosphate buffered saline |
| β-ME | = | β-mercaptoethanol |
| MOI or m.o.i. | = | multiplicity of infection |
| PFU | = | plaque forming units |
| hr | = | hour |
| ° C. | = | degree Celsius |

General Method
Cells and Virus

Human embryo kidney 293 (HEK 293), Vero (African green monkey kidney) cells, and mouse fibroblast L-929 cells were provided by the manufacturer BioReliance Corporation (Rockville, Md.). HEK 293 cells were grown in a culture medium containing 10% heat-inactivated horse serum and 90% of the following mixture: Eagle's minimum essential medium with 2 mM L-glutamine and Earle's Balanced Salt Solution adjusted to contain 1.5g/L sodium bicarbonate, 0.1 mM non-essential amino acids, and 1.0 mM sodium pyruvate. Mouse L-929 and Vero cells were propagated in a culture medium containing 10% FBS and 90% of the following mixture: Eagle's minimum essential medium with 2 mM L-glutamine and Earle's Balanced Salt Solution adjusted to contain 1.5g/L sodium bicarbonate, 0.1 mM non-essential amino acids, and 1.0 mM sodium 15% pyruvate.

The 293/SF cells were grown in 293 Serum Free Medium (Life Technologies, Rockville, Md.) supplemented with 4 mM L-glutamine at 36° C.±2° C., 6%±2% $CO_2$ and 80% ±5% relative humidity in spinner flasks at an impeller speed of 35–40 rpm.

The Dearing strain of reovirus serotype 3 used in these studies was propagated in suspension cultures of L-929 cells purified according to Smith (Smith et al., 1969) with the exception that β-mercaptoethanol (β-ME) was omitted from the extraction buffer. The particle/PFU ratio for purified reovirus was typically 100/1.

Infection of Monolayer Cells and Quantitation of Virus

Confluent monolayers of HEK 293, Vero, and L-929 cells were grown in 24-well plates and infected with a reovirus at known multiplicities of infection. After 1 hr incubation at 37° C., the monolayers were washed with warm media and then incubated in their culture medium. At various time points postinfection, a mixture of NP-40 and sodium deoxycholate was added directly to the media on the infected monolayers to final concentrations of 1% and 0.5%, respectively. The lysates were then harvested and virus yields were determined by plaque titration on L-929 cells and expressed as $Log_{10}TCID_{50}$/ml.

Infection of Suspension Cells

293/SF cells were grown to $10^6$/ml and infected with the reovirus. The culture was allowed to grow until the color of the medium turned from red to orange, or until the viability of the cells dropped to the desired level as evidenced by a viable cell count. Viable cell counts can be performed under the microscope for cells that do not show a cytopathic effect, which is indicated by the cells becoming swollen and granular in appearance and the cell clumps breaking apart. Viable cell counts can also be performed by a viable stain as commonly used in the art.

Traditional Method of Extraction and Purification of Virus

When the desired cell viability level was reached, the cells were pelleted in a centrifuge and resuspended in 10 mM Tris, pH 7.4, 250 mM NaCl and 0.1% Triton X-100. The cells were then lysed by freeze-thawing and kept on ice for 20–40 minutes with periodical vortexing to mix and lyse the cells. The suspension was extracted with an equal volume of pre-chilled Freon® (1,1,2-trichloro-1,1,2-trifluoro-ethane) by vortexing for 10 minutes, followed by centrifugation at 2500 rpm for 10 minutes at 4° C. to separate the difference phases. The aqueous (top) phase was removed and re-extracted twice as described above, and the virus was pelleted by ultracentrifugation at 25,000 rpm for one hour at 4° C.

The pellet was resuspended in PBS and the virus was purified by a cesium chloride step gradient. The gradient contained two layers of CsCl solutions (1.20g/ml and 1.4g/ml, respectively) prepared in 10 mM Tris (pH 7.4). The virus suspension was loaded on top of the gradient and centrifuged in a SW 28.1 rotor at 26,000 rpm for 2 hours at 4° C. The viral band (the lower of the two bands because the upper band contained empty capsids) was harvested and dialyzed against sterile PBS.

Example 1

Determination of Optimal Cell Lines for the Production of Reovirus

To determine whether there were differences between susceptible cell lines in the amount of reovirus produced as a consequence of infection, a number of different cell lines that exhibited reovirus susceptibility were assayed for relative amount of reovirus produced. Of particular interest were those cell lines that had been approved by various regulatory authorities for the production of a biological agent. Accordingly, HEK 293, Vero, and L-929 cells were exposed to reovirus, and their ability to produce reovirus was compared.

Quantitation of viral production was accomplished by harvesting infected cells and their growth media at various time points post infection. The lysates produced were subsequently subjected to plaque titration analysis to determine the viral yield, which is expressed as titer ±95% CI ($Log_{10}TCID_{50}$/ml) in Table 1 below. The results indicate that, whereas all of the tested cells were susceptible to reovirus infection, there were considerable differences in the amount of virus produced in each of these cells lines.

TABLE 1

Time Course of Viral Yield of Various Cell Lines
(expressed as titer ± 95% CI in $Log_{10}TCID_{50}$/ml)

| TIME | HEK 293 | Vero | L929 |
| --- | --- | --- | --- |
| 24 HOURS | 8.30 ± 0.51 | 4.80 ± 0.35 | 6.68 ± 0.24 |
| 36 HOURS | 9.05 ± 0.43 | 5.55 ± 0.32 | 7.93 ± 0.40 |
| 48 HOURS | 9.55 ± 0.49 | 6.68 ± 0.40 | 8.55 ± 0.49 |
| 72 HOURS | 9.30 ± 0.43 | 8.18 ± 0.36 | 9.05 ± 0.32 |
| 96 HOURS | 9.80 ± 0.35 | 9.93 ± 0.59 | 9.30 ± 0.43 |

The results show clearly that HEK 293 cells are the most efficient cells to produce reovirus. Further, the HEK 293 cells produced more virus earlier, allowing for shortened production times for the manufacture of the reovirus.

Example 2

Effect of Starting Multiplicity of Infection on Final Viral Production

To determine whether the starting multiplicity of infection determines final viral output, HEK 293 cells were infected with a range of starting multiplicities of infection (m.o.i.) between 1 and 0.1. Our results, shown in Table 2, indicate that there is indeed a relationship between the starting m.o.i. and the final viral production. A starting m.o.i. of less than 1 is optimal for the large scale manufacture of reovirus.

TABLE 2

Effect of M.O.I. on Viral Production
(expressed as titer ± 95% CI in $Log_{10}TCID_{50}$/ml)

| TIME | 1.0 MOI | 0.5 MOI | 0.1 MOI |
| --- | --- | --- | --- |
| 24 HOURS | 9.18 ± 0.36 | 8.55 ± 0.43 | 7.68 ± 0.24 |
| 36 HOURS | 8.92 ± 0.52 | 9.30 ± 0.43 | 9.37 ± 0.48 |
| 48 HOURS | 9.55 ± 0.43 | 10.30 ± 0.37 | 9.68 ± 0.50 |
| 72 HOURS | 9.55 ± 0.32 | 9.93 ± 0.40 | 9.18 ± 0.40 |
| 96 HOURS | 9.80 ± 0.00 | 10.30 ± 0.43 | 10.18 ± 0.36 |

Furthermore, our results demonstrate that there is also an optimal time at which to harvest the cells, which will be important. We found that viral production is greatest after 24 hours. This is not surprising as prior to 24 hours, there would be insufficient time for adequate viral protein synthesis and the assembly of the mature virion. More surprising is the observation of a decrease in virus quantity at the 72 hour point followed by a marked increase in the number of infectious particles at the 96 hour time point. It is presumed that this slight decrease at 72 hours is likely due to proteolytic degradation of the virus followed by a second round of virus replication at the 96 hour point.

Example 3

Evaluation of Virus Extraction Procedures

Initially, we followed traditional methods to extract and purify viral particles as described in Materials and Methods. Briefly, the cells were disrupted by freeze-thawing and extracted by Freon three times. The viral particles were then purified with a CsCl gradient and ultracentrifuge. However, this protocol was too tedious and time consuming for large scale virus production. We therefore tested several other extraction methods as described below in order to optimize the harvest conditions for large scale suspension cultures.

Reovirus was grown in suspension cultures of HEK 293 cells for 24, 48 or 72 hours with constant agitation. Thereafter, a detergent, such as Triton X-100, Tween 20, NP-40 or sodium deoxycholate (Na-DOC), was added to the culture to the final concentrations indicated for each experiment in Table 3. The culture continued to be agitated for 10 or 60 minutes at 25° C. or 37° C. Then an aliquot was taken from the culture, and the viral yield was determined by plaque titration on L-929 cells and expressed as $Log_{10}TCID_{50}$. Also tested was a freeze-thaw method wherein the culture was frozen and thawed in order to disrupt the cells, without any detergent. In the "no treatment" experiment, an aliquot was taken directly from the culture and viral yield was determined.

TABLE 3

Effects of different extraction methods on viral yield

| Time | Sample | Viral Yield ± CI ($Log_{10}TCID_{50}$) |
| --- | --- | --- |
| | Spiking virus control #1 | 8.30 ± 0.37 |
| | Spiking virus control #2 | 7.68 ± 0.40 |
| | Spiking virus control #3 | 7.93 ± 0.24 |
| | Certified titer of virus control | 7.99 ± 0.24 |
| | Negative control | No virus detected |
| 24 Hours | 25° C., 10 min, 0.1% TX-100 | 10.67 ± 0.24 |
| | 25° C., 10 min, 1% Tween-20 | 10.42 ± 0.40 |
| | Freeze/thaw | 10.00 ± 0.37 |
| | No treatment | 9.88 ± 0.36 |
| 48 Hours | 25° C., 10 min, 0.1% TX-100 | 10.04 ± 0.43 |
| | 25° C., 10 min, 0.3% TX-100 | 10.42 ± 0.52 |
| | 25° C., 10 min, 1% Tween-20 | 10.17 ± 0.36 |
| | 25° C., 10 min, 3% Tween-20 | 9.79 ± 0.32 |
| | 25° C., 10 min, 0.1% Na-DOC | 10.42 ± 0.50 |
| | 25° C., 10 min, 1% NP-40 | 9.77 ± 0.32 |
| | 25° C., 60 min, 0.1% TX-100 | 10.17 ± 0.44 |
| | 25° C., 60 min, 1% Tween-20 | 9.92 ± 0.36 |
| | 37° C., 10 min, 0.1% TX-100 | 10.42 ± 0.40 |
| | 37° C., 10 min, 1% Tween-20 | 10.29 ± 0.32 |
| | 37° C., 60 min, 0.1% TX-100 | 10.42 ± 0.50 |
| | 37° C., 60 min, 1% Tween-20 | 9.42 ± 0.66 |
| | Freeze/thaw | 10.38 ± 0.24 |
| | No treatment | 10.25 ± 0.32 |
| 72 Hours | 25° C., 10 min, 0.1% TX-100 | 11.29 ± 0.75 |
| | 25° C., 10 min, 1% Tween-20 | 9.79 ± 0.32 |
| | Freeze/thaw | 10.63 ± 0.24 |
| | No treatment | 10.13 ± 0.44 |

These results indicate that Triton X-100, Tween 20, Na-DOC or NP-40 can all be used to extract reovirus from HEK 293 cell cultures with viral yields better or comparable to that of the freeze-thaw method. Noticeably, procedures employing Triton X-100 generally produced more virus than procedures using the other two non-ionic detergents, Tween 20 and NP-40, by about 2 fold. Na-DOC, the only ionic detergent tested, produced about the same number of infectious virus as 0.3% Triton X-100 under these conditions. The concentration of Triton X-100 was optimized in further studies, which indicate that a final concentration of 1% Triton X-100 in the extraction mixture yielded the highest viral production.

In addition, it is worth noting that by using a detergent to lyse the cells instead of freeze-thaw, the extraction procedure can be conveniently performed at 25° C. or even 37° C., and the yield of infectious viral particles was not affected. This is in contrast to the traditional practice of performing the entire virus extraction procedure in the presence of protease inhibitors at a low temperature, usually 4° C., in order to preserve functional proteins. Therefore, viruses can be extracted from cultured cells by a simple and convenient procedure which greatly improves large scale virus productions.

Although viral yields from the "no treatment" experiments were quite high, suggesting that many viral particles might have been released into the culture medium prior to extraction, the detergent treatment further increased the yield by about 10 fold. The increase in yield by detergent treatment was particularly evident at 24 and 72 hours post infection. At the 48 hour time point, however, detergent extraction did not much increase viral yield. It therefore appears that most of the virus was cell associated at the 24 and 72 hour time points but not at the 48 hour point. This observation is consistent with the previous discussion that proteolytic degradation may occur at a mid point in the course of the culture, which is followed by a second round of viral replication.

Subsequent to the extraction procedure described above, cell debris can be removed by simple methods such as filtration or centrifugation, and the resulting virus can be used for clinical administration. If cell debris is removed by filtration, the filtrate can optionally be concentrated, for example, by ultrafiltration, to reduce the volume of the virus preparation. Iron content of the filtrate or concentrated viral preparation can be further adjusted, for example, by ion exchange chromatography or dialysis.

We claim:

1. A method of producing mammalian reovirus from a culture of cells, comprising the steps of:
   (a) providing a culture of human embryo kidney 293 (HEK 293) cells which has been infected by the reovirus;
   (b) extracting the reovirus from the HEK 293 cells by adding a detergent to the culture and incubating for a period of time; and
   (c) collecting the reovirus.

2. The method of claim 1 wherein the detergent is selected from the group consisting of octoxynol-9 to 10, polyethylene glycol sorbitan monolaurate, octylphenoxy polyethoxy ethanol and sodium deoxycholate.

3. The method of claim 1 wherein the detergent is selected from the group consisting of octoxynol-9 to 10, polyethylene glycol sorbitan monolaurate, and octylphenoxy polyethoxy ethanol.

4. The method of claim 3 wherein the detergent is octoxynol-9 to 10.

5. The method of claim 4 wherein the final concentration of octoxynol-9 to 10 is 1%.

6. The method of claim 1 wherein the incubation of step (b) is performed at or above ambient temperature.

7. The method of claim 6 wherein the incubation of step (b) is performed at about 25° C.

8. The method of claim 6 wherein the incubation of step (b) is performed at about 37° C.

9. The method of claim 1 wherein the culture is incubated with the detergent in step (b) for 60 minutes or less.

10. The method of claim 9 wherein the culture is incubated with the detergent in step (b) for 30 minutes or less.

11. The method of claim 10 wherein the culture is incubated with the detergent in step (b) for 10 minutes.

12. The method of claim 1 wherein the mammalian reovirus is a human reovirus.

13. The method of claim 12 wherein the human reovirus is a serotype 3 virus.

14. The method of claim 13 wherein the serotype 3 reovirus is the Dearing strain.

15. The method of claim 1 wherein the HEK 293 cells are grown in suspension.

16. The method of claim 1 wherein step (c) comprises removing cell debris by filtration.

17. The method of claim 16 further comprising a step of concentration after filtration.

18. A method of producing infectious mammalian reovirus, comprising:
   (a) providing a culture of HEK 293 cells which has been infected by the reovirus;
   (b) extracting the virus from the cells by adding octoxynol-9 to 10 to the culture and incubating at about 25° C. to about 37° C. for about 10 minutes; and
   (c) collecting the reovirus.

19. The method of claim 18 wherein step (c) comprises removing cell debris by filtration and concentrating the filtrate.

* * * * *